(12) United States Patent
Allison

(10) Patent No.: US 6,426,051 B1
(45) Date of Patent: Jul. 30, 2002

(54) OIL BURNING LAMP ADAPTED TO DISPERSE FRAGRANCE

(75) Inventor: Gerald Herbert Allison, Lake Hiawatha, NJ (US)

(73) Assignee: Noville, Inc., South Hackensack, NJ (US)

( * ) Notice: Subject to any disclaimer, the term of this patent is extended or adjusted under 35 U.S.C. 154(b) by 0 days.

(21) Appl. No.: 09/569,027

(22) Filed: May 11, 2000

(51) Int. Cl.⁷ .................................................. A62B 7/08
(52) U.S. Cl. ........................... 422/125; 422/5; 422/123; 422/125; 122/366; 431/320; 431/321; 431/322; 431/323; 431/324
(58) Field of Search ........................... 422/5, 123, 125; 431/320, 321, 322, 323, 324; 122/366

(56) References Cited

U.S. PATENT DOCUMENTS

| | | | | |
|---|---|---|---|---|
| 3,872,280 A | * | 3/1975 | Van Dalen | 422/125 |
| 3,898,039 A | * | 8/1975 | Lin | 422/125 |
| 4,116,266 A | | 9/1978 | Sawata et al. | 165/105 |
| 4,568,270 A | * | 2/1986 | Marcus et al. | 422/125 |
| 4,903,761 A | | 2/1990 | Cima | 165/104.25 |
| 5,468,497 A | * | 11/1995 | Katsuda | 422/125 |
| 5,647,053 A | | 7/1997 | Schroeder et al. | 392/390 |
| 5,650,126 A | | 7/1997 | Taoda et al. | 422/122 |
| 5,840,246 A | * | 11/1998 | Hammons et al. | 422/125 |
| 6,333,009 B1 | | 12/2001 | Allison | 422/125 |

* cited by examiner

Primary Examiner—Robert J. Warden, Sr.
Assistant Examiner—Imad Soubra
(74) Attorney, Agent, or Firm—Kenyon & Kenyon

(57) ABSTRACT

The present invention is directed to an oil lamp adapted to disperse fragrance. More specifically, the present invention provides a lamp having a container with one or more vent holes, through which fragrance molecules volatilized from scented fuel within the container may escape.

13 Claims, 4 Drawing Sheets

OIL BURNING LAMP ADAPTED TO DISPERSE FRAGRANCE

FIELD OF INVENTION

The present invention relates to an oil burning lamp adapted to disperse fragrance. One embodiment of the invention includes vent holes that allow fragrance to escape from the lamp. Another embodiment of the invention includes a heat transfer system that heats oil within the lamp, thereby increasing the amount of fragrance volatilized from the oil.

BACKGROUND OF THE INVENTION

Light sources such as candles and gel pots are commonly used as decorative light sources, and to disperse fragrances. These light sources include a wick extending from the candle or gel. A flame at the end of the wick is sustained by wax or gel that has been melted by the heat of the flame. In particular, the heat of the flame melts a small pool of the candle body material around the base of the exposed portion of the wick. This molten material is then drawn up through and along the wick by capillary action to fuel the flame. Candles and gel pots may also be used to effectively disperse fragrance molecules included in the wax or gel. Such fragrance is dispersed when it is volatilized from the liquid pool into the surrounding air.

Conventional oil lamps differ from candles and gel pots in that the oil is held in a container with no access to the outside except through the wick, which protrudes from the container through a wick aperture. Such lamps are typically filled through the wick aperture with the wick temporarily removed, or through a filling hole that can be sealed or plugged prior to lighting the oil lamp. When lit, a flame on the end of the wick outside of the container is sustained by oil rising through the wick by capillary action. The closed container has several advantages. For example, the risk of a spill is reduced. Also, there is little risk that oil within the closed container will be accidentally ignited. However, the closed container also prevents fragrance molecules volatilized from the oil from escaping the container into the surrounding air. As a result, conventional oil lamps do not effectively disperse fragrance. Although fragrance molecules may rise through the wick to the flame, the amount of such molecules that rise through the wick and survive combustion are not sufficient to effectively disperse fragrance.

Oils for use in lamps often contains fragrance molecules. However, the purpose of the fragrance is to entice the consumer at the point of sale, and to suppress unpleasant odors associated with certain types of oil, such as kerosene. The fragrance is not dispersed during burning in a conventional oil burning lamp.

Because the oil used in oil burning lamps is liquid at room temperature, conventional oil lamps are not designed to effectively heat oil in the container. Indeed, such heating may have been undesirably viewed as creating a higher risk of uncontrolled fires. Some conventional wicks do include metal cores for the purpose of supporting the wick. However, these cores may be too small to effectively conduct heat from the flame to the oil. Moreover, they do not have a significant area exposed to either the heat of the flame or the oil within the lamp, because they are encased by the wick, which restricts their ability to conduct heat from the wick to the oil. Such cores were previously made of lead. However, due to health concerns associated with lead, zinc is commonly used today.

Conventional oil lamps may be made of a variety of substances, including glass and ceramic. Glass is generally preferred for its decorative qualities.

SUMMARY OF THE INVENTION

The present invention is directed to an oil lamp adapted to disperse fragrance.

More specifically, a first embodiment of the present invention relates to a lamp having a container with one or more vent holes, through which fragrance molecules volatilized from oil within the container may escape.

A second embodiment of the invention relates to a heat transfer system adapted to transfer heat from the flame of the oil lamp to oil contained within the oil lamp. The heat transfer system has a heat absorbing region disposed near the flame, and a heat dissipating region disposed within the container, connected to the heat absorbing region by a thermally conductive path. Heating the oil enhances the amount of fragrance volatilized from the oil.

Further objectives and advantages of the subject invention will be apparent to those skilled in the art from the detailed description of the disclosed invention.

DETAILED DESCRIPTION

Figure 1:
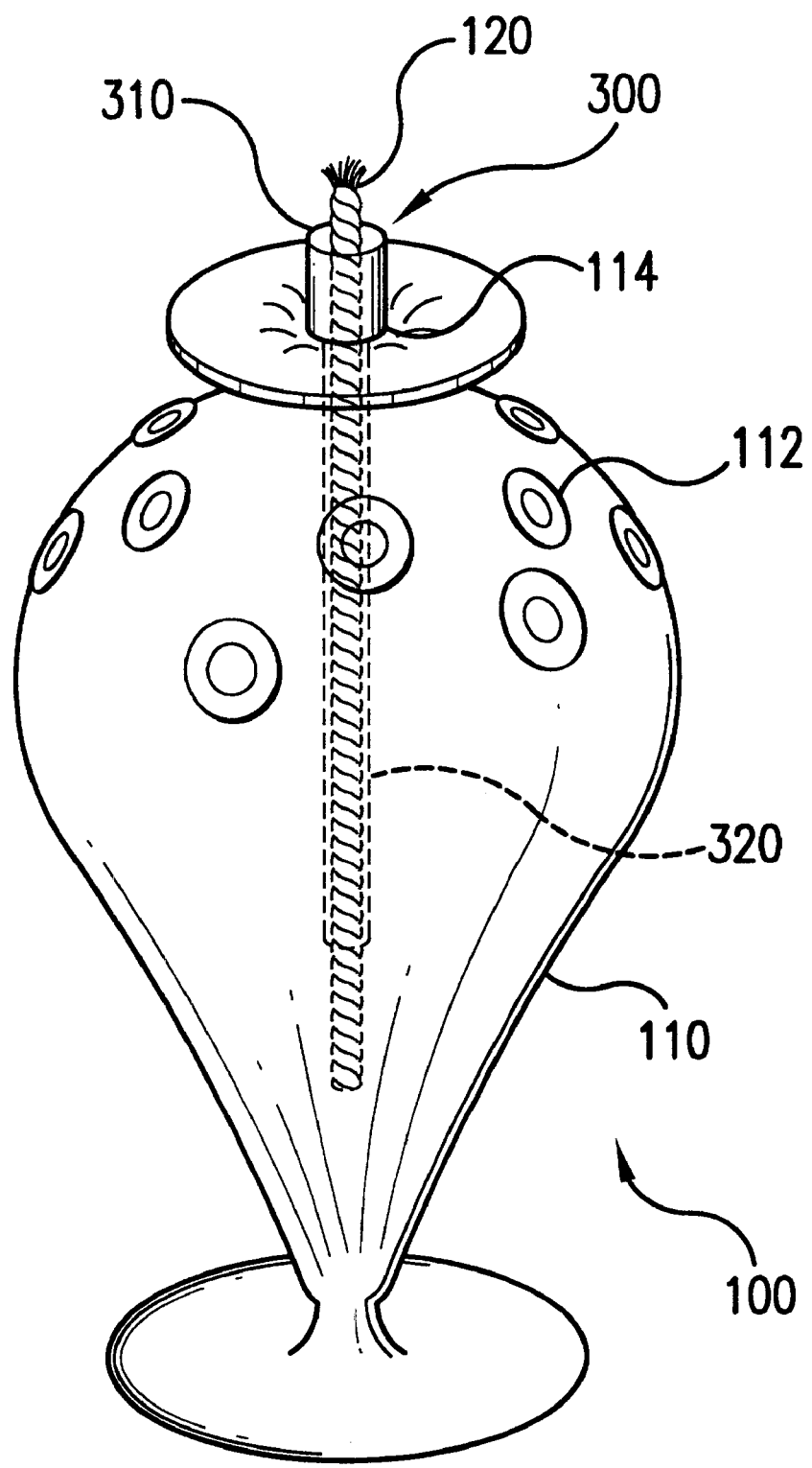
FIG. 1 shows an oil lamp in accordance with the present invention.

The subject invention will now be described in detail for specific preferred embodiments of the invention, it being understood that these embodiments are intended only as illustrative examples and the invention is not to be limited thereto.

The present invention provides an oil burning lamp adapted to disperse fragrance. In particular, the lamp may have vent holes through which fragrance molecules volatilized from the oil inside the lamp may diffuse, such that the lamp emits fragrance. This diffusion may occur both when the lamp is lit, and when the lamp is not lit.

The lamp may also have a heat transfer system adapted to transfer heat from the burning flame at the end of the wick to the oil within the lamp. Heating the oil within the lamp is beneficial in that more fragrance will be volatilized from the oil.

Vent Holes

A first embodiment of the present invention has vent holes in the container allow fragrance volatilized from oil within the container to escape the container. These vent holes are located on the upper portion of the container, preferably the upper third of the container. Locating the vent holes any lower undesirably limits the amount of oil that may be filled into the container without significant risk of leaking or spilling. Preferably, the vent holes are located on a top portion of the container that is relatively horizontal, i.e., less than about 45°, to reduce the risk of accidentally filling the container to a level over the vent holes. While the vent holes may be any size or shape, they are preferably between about 1 mm and 10 mm in diameter, i.e., have a cross sectional area of about 0.75 square mm. and 75 square mm. Smaller vent holes may reduce the amount of fragrance dispersed from the lamp. Larger vent holes may increase the risk of rapid oil spills, or ignition of oil within the container. More preferably, the vent holes are about 5 mm in diameter (18.75 square mm). Preferably there are a plurality of vent holes, having an aggregate area of at least about 180 square mm, to ensure adequate diffusion of volatilized fragrance molecules through the vent holes. A plurality of vent holes advantageously allows any currents in the air surrounding the lamp to pass through the lamp, enhancing the transport of fragrance molecules from inside the lamp.

Conventional oil burning lamps are not adapted to disperse fragrance from a scented oil because there is no route for the fragrance to escape from the lamp. While the oil does rise through the wick to the flame, the fragrance typically does not survive combustion in sufficient quantities to effectively disperse fragrance. The vent holes overcome this shortcoming of conventional oil lamps, allowing the lamps to disperse fragrance. Fragrance may be dispersed through the vent holes both when the lamp is lit, and when it is not lit.

Preferred fragrances include those commercially available from Noville Corp. of South Hackensack, N.J. Such fragrances are preferably added to lamp oil in an amount of about 0% to 30% by weight, more preferably in an amount of about 2% to 10%, and most preferably about 10%, with the amount selected so as to achieve the desired throwing power and to mask any unpleasant odor associated with the fuel. The amount of fragrance included in the oil may depend upon the particular fragrance involved, as well as the particular configuration of the oil lamp.

The lamp of the present invention may also use other conventional materials as fuel, as known to the art. The n-parafinic hydrocarbons, such as NORPAR® 15 (commercially available from the Exxon Corporation), are preferred. This class of solvents is preferred because they produce very little soot or smoke, do not have an unpleasant kerosene odor, and have a high flash point. For example, the flash point of NORPAR® 15 is about 242° F., as compared to about 150° C. to 160° F. for kereosene. The amount of fragrance used with such solvent is about the same as that used with kerosene, although it may be possible to use lower amounts because there is no unpleasant kerosene odor to mask.

Heat Transfer System

A second embodiment of the present invention has a heat transfer system adapted to transfer heat from a flame at the end of the wick to the oil within the lamp. Heating the oil in this manner volatilizes more fragrance from the oil, thereby enhancing the amount of fragrance dispersed by the lamp when it is lit.

The heat transfer system has a heat absorbing region disposed near the end of the wick where the flame is located, such that the heat absorbing region as exposed to significant heat from the flame. This heat absorbing region preferably has a significant surface area near the flame, such that heat is effectively absorbed. Preferably, the heat absorbing region has a surface area of at least about 140 square cm, and more preferably of at least about 280 square mm. (based on the interior surface area of a cylinder with a height of 15 mm and an interior diameter of 6 mm). For example, the heat absorbing region may be a cylinder disposed around the flame, a plate immediately below the flame, several smaller wires decoratively positioned near the flame, or any other configuration adapted to absorb heat from the flame. Preferably, the heat absorbing region is directly exposed to flame. However, the heat absorbing region does is not necessarily so exposed, so long as it is close enough to the flame to absorb significant heat.

The heat transfer system also has a heat dissipating region within the container, which dissipates heat into the oil in the container. The heat dissipating region is preferably exposed directly to the oil, without being blocked by the wick. The heat dissipating region may have a number of forms. Preferably, the heat dissipating region is a tube disposed around the wick. Although a cylindrical tube may be the easiest to fabricate, other shapes may be used, such as tubes having square or hexagonal cross sections. This design allows for direct exposure to the oil, easy assembly, and use with conventional wicks. The heat dissipating region may also be a metal core within the wick. However, such an embodiment is less efficient, and is preferably combined with some additional heat dissipating region outside of the wick, such as a disk towards the bottom of the container. The heat dissipating may also have different forms, provided that it serves the purpose of dissipating heat into oil within the lamp.

The heat absorbing region is connected to the heat dissipating region by a thermally conductive path. Preferably, this is achieved by making the heat transfer system out of a single piece of thermally conductive material. Based on the prototype, the thermally conductive path preferably has a thermal conductivity of at least 0.007 W/°K (based on a copper cylinder with a 4 mm outer diameter, 2 mm inner diameter, cross sectional area of 9.4 square mm, and 5 cm in length). However, it is believed that significantly smaller thermal conductivities will work. "Thermal conductivity" as used herein means the cross sectional area of the heat conductive path multiplied by the thermal conductance of the material, divided by the length. Thermal conductance data is readily available from sources such as the CRC— about 4.01 W/cm–°K for Cu, 1.16 for Zn, 0.666 for Sn, and 2.37 for Al.

The heat transfer system may be made from any suitable material or materials adapted to absorb, conduct, and dissipate heat. Preferably, the heat transfer system is made of a metal, such as copper, aluminum, zinc, tin, brass, platinum, silver or gold. Considerations included in choosing the particular material include cost, heat absorption and transfer properties, and appearance.

Preferably, the heat transfer system has only minimal exposure outside of the oil container, because it may become hot during use. Keeping most of the heat transfer system inside of the container minimizes the risk of a user touching a hot surface, and also increases the efficiency of heat transfer to the oil by reducing the amount of heat dissipated into the surrounding atmosphere. In particular, the heat dissipating region and the conductive path are preferably located entirely within the container. However, the heat absorbing region is preferably disposed outside of the container, because the flame from which it absorbs heat is also disposed outside of the container. Depending on the design, it may also be necessary to locate at least a small portion of the conductive path outside of the container.

Preferred dimensions and parameters are given above. However, significantly different combinations of dimensions and parameters may be used. The important feature of the heat transfer system is that is as able to effectively transfer heat from the flame to oil or solvent within the lamp. Preferably, the heat transfer system is adapted to heat fuel within the lamp to a temperature at least 5° C. above the ambient temperature (typically a room temperature of about 25° C.). Such a temperature difference is significant enough to noticeably enhance the volatilization of fragrance from the fuel. More preferably, the heat transfer system is adapted to heat fuel within the container to a temperature at least about 25° C. above the ambient temperature. Such a temperature difference will not result in unsafe fuel temperatures for a lamp at room temperature, and will significantly enhance the volatilization of fragrance from the fuel. Preferably, the heat transfer system does not reach temperatures above 100° C., and does not heat the fuel to temperatures higher than about 60° C. (a typical temperature for molten wax in the pool of a candle). Higher temperatures may pose a safety risk.

This invention will now be described in detail with respect to showing how certain specific representative embodiments thereof will be made, the materials, apparatus and process steps being understood as examples that are intended to be illustrative only. In particular, the invention is not intended to be limited to the methods, materials, conditions, process parameters, apparatus and the like specifically recited herein.

EXAMPLE OF THE INVENTION

Several embodiments of the present invention are specifically illustrated and/or described herein. However, it will be appreciated that modifications and variations of the those embodiments are encompassed by the above teachings as well as the attached claims.

FIG. 1 shows an oil lamp 100 in accordance with the present invention. Lamp 100 may be any size, but a height of about 10 cm is typical for decorative oil burning lamps. A container 110 is adapted to hold the oil burned by the lamp. Container 110 has vent holes 112 on its upper region. Container 110 also has a wick aperture 114 at its apex. A heat transfer system 300 is inserted into wick aperture 114. Heat transfer system 300 has a heat absorbing region 310 and a heat dissipating region 320. In this particular embodiment, heat absorbing region 310 is a cylinder approximately 1 cm in diameter and 1.5 cm in height. Tube 320 is a cylindrical tube about 9 cm in length and 0.4 cm in diameter, attached to heat absorbing region 310. A wick 120 is disposed within heat transfer system 300. The walls of heat absorbing region 310 and tube 320 are approximately 2 mm and 1 mm in thickness, respectively.

When container 110 contains oil, a part of tube 320 is submerged in the oil. The submerged part of tube 320 is the heat dissipating region. The part of tube 320 that is not submerged in oil provides a thermally conductive path from heat absorbing region 310 to the heat dissipating region. When lamp 100 is lit, the flame is at the end of wick 120 that is near heat absorbing region 310. Heat absorbing region 310 absorbs heat from the flame, which then moves along the thermally conductive path to the heat dissipating region of tube 320. The heat is then transferred to the oil within the lamp. As a result, fragrance molecules in the oil are more readily volatilized.

Figure 2:
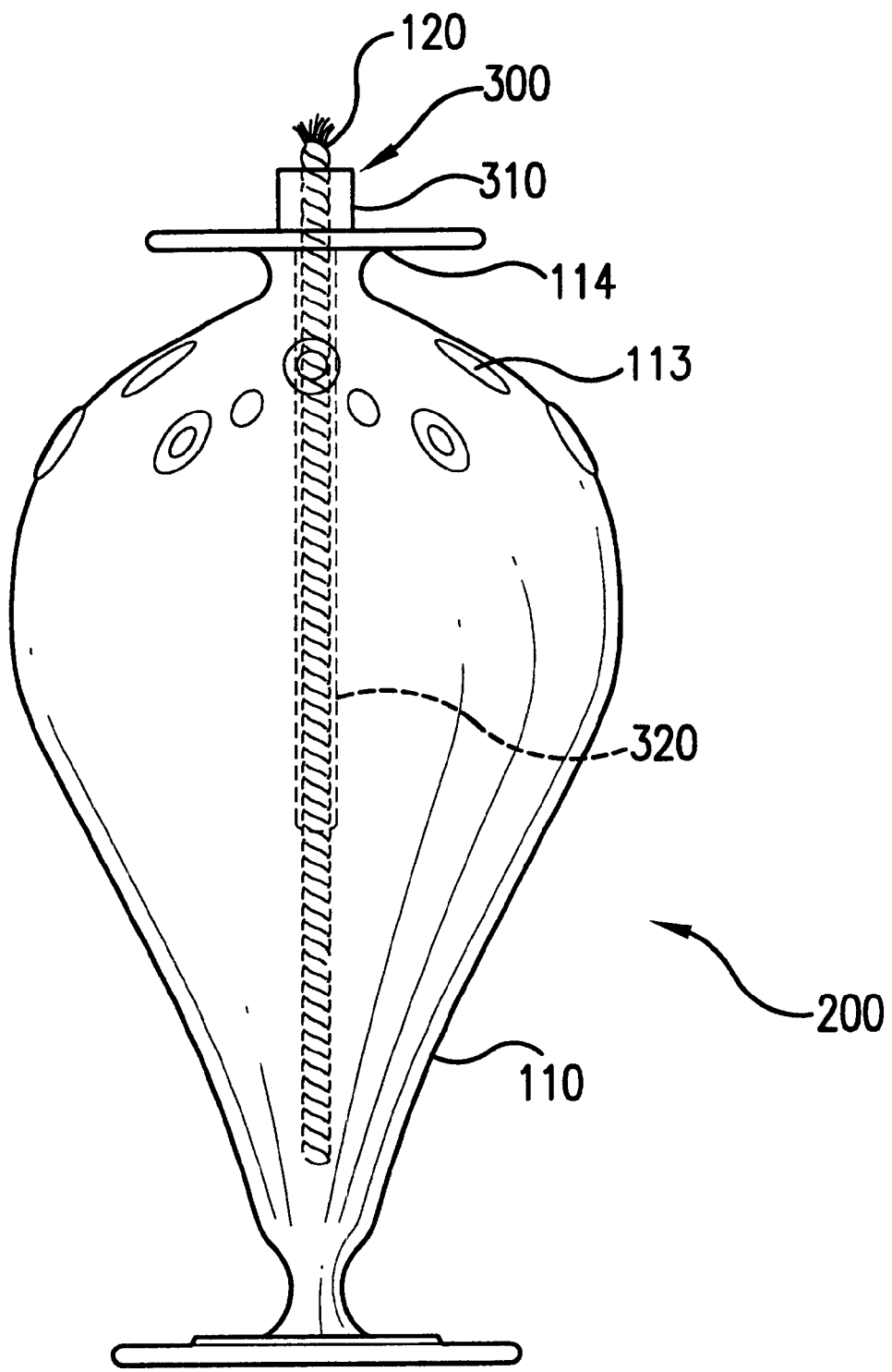
FIG. 2 shows a side view of an oil lamp in accordance with the present invention.

FIG. 2 shows a side view of an oil lamp 200 in accordance with the present invention. Lamp 200 is very similar to lamp 100, but has slightly different vent holes 113.

Figure 3:
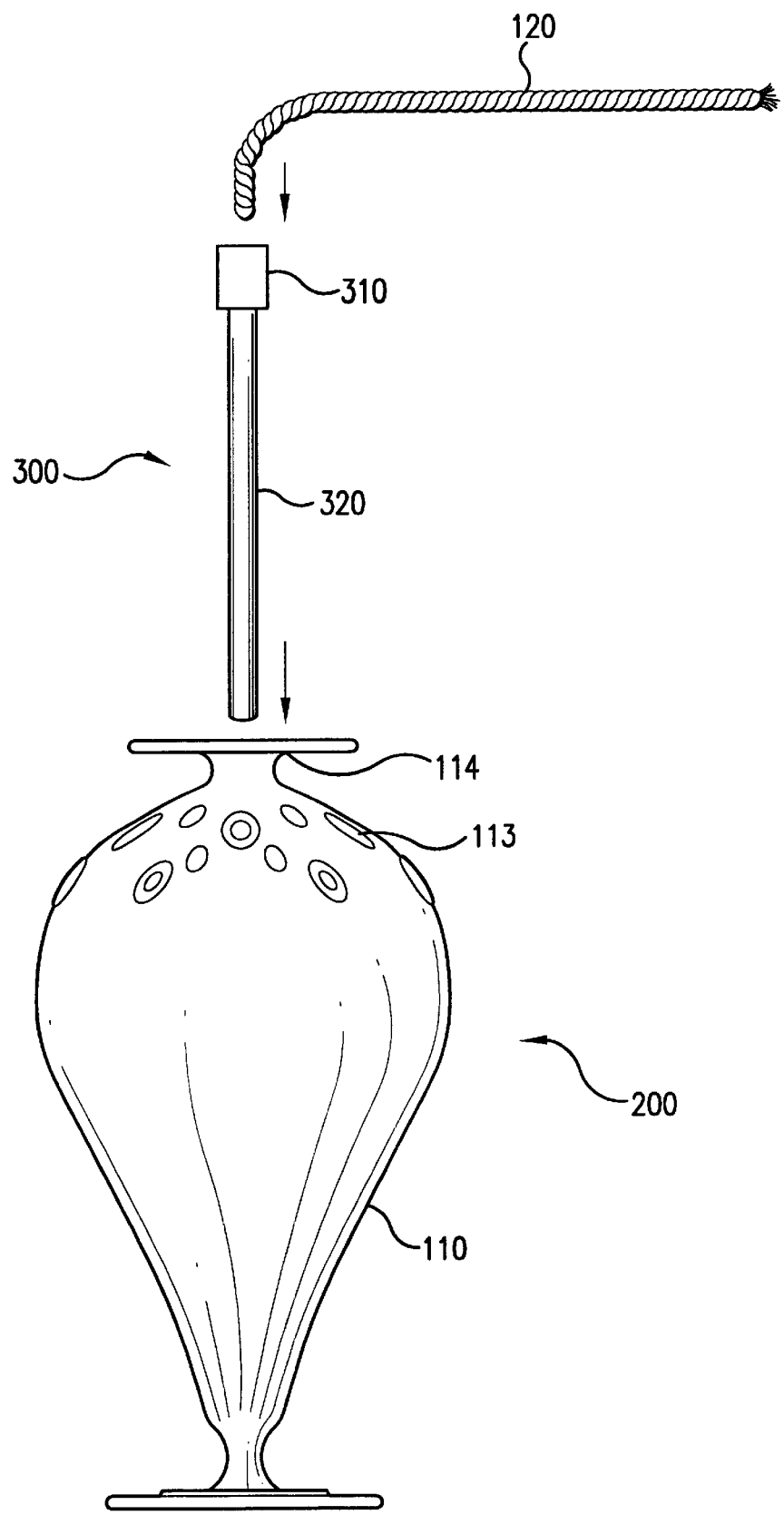
FIG. 3 shows the oil lamp of FIG. 2, with the wick and heating system separated from the oil container.

FIG. 3 shows a side view of oil lamp 200 of FIG. 2, with wick 120 and heat transfer system 300 separated from container 110. With wick 120 and heat transfer system 300 removed, container 110 may be conveniently filled with oil through wick aperture 114.

Figure 4:
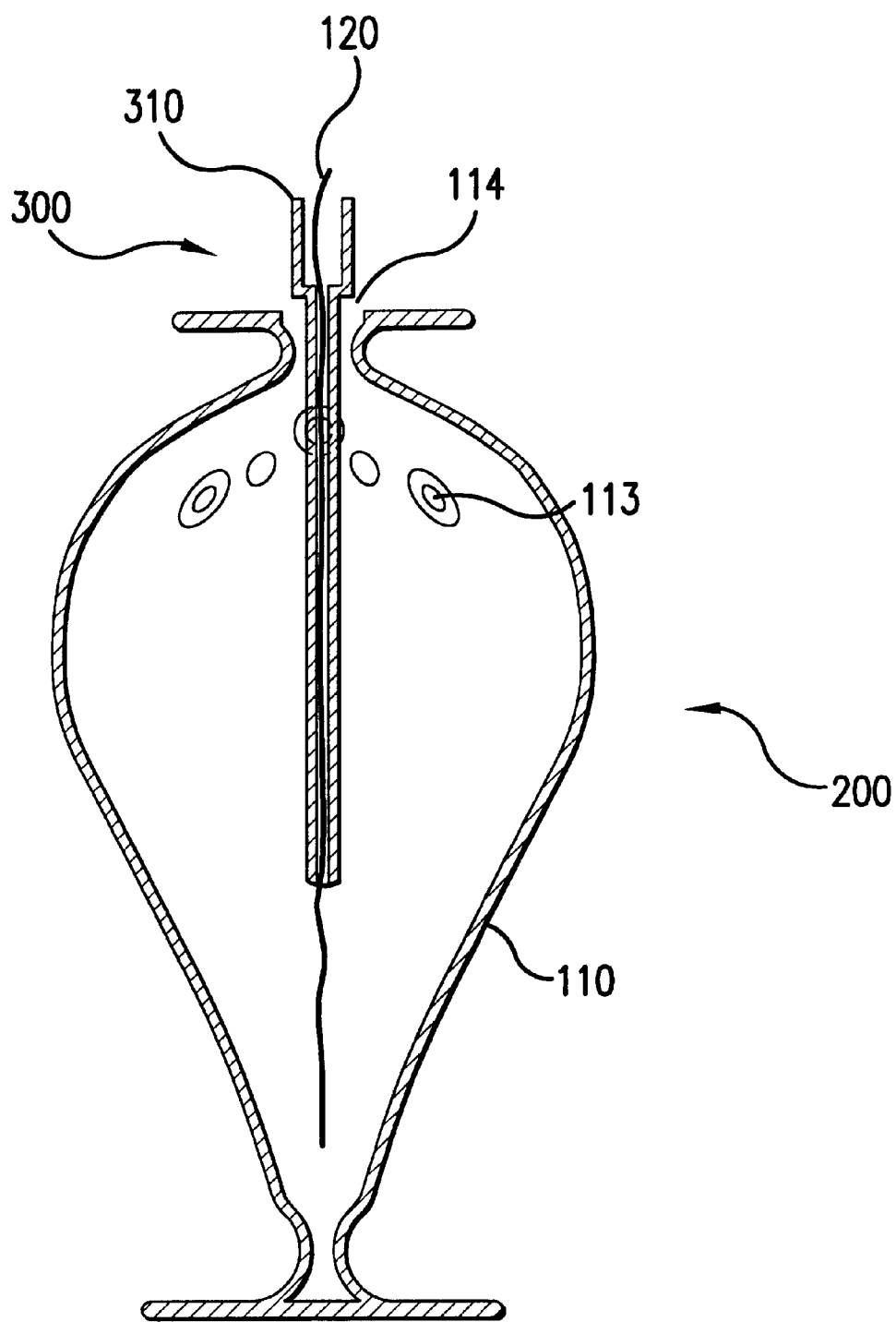
FIG. 4 shows a cross sectional view of the oil lamp of FIG. 2.

FIG. 4 shows a cross sectional view of oil lamp 200 of FIG. 2. Container 110, wick 120, wick aperture 114, heat transfer system 300, heat absorbing region 310 and tube 320 function in the same manner as described with respect to FIG. 2.

The particular design of heat transfer system 300 as illustrated in FIGS. 1–4 has a number of significant advantages. Heat transfer system 300 may be easily fabricated from a single piece of metal, or by attaching two cylindrical metal pieces of different diameter. The fact that heat absorbing region 310 is wider than tube 320 allows heat absorbing region 310 to support heat transfer system 300 by resting on container 110 around wick aperture 114, while tube 320 extends into container 110. Heat transfer system 300 may therefore be readily inserted into and removed from lamp 200.

A lamp similar to that of FIG. 1 was constructed and filled with room temperature oil. The lamp was placed in a room temperature environment and lit. A short time after lighting the lamp, the temperature of the oil in the lamp was measured at about 53° C., and the heat dissipating region had a temperature of about 100° C.

What is claimed is:
1. A lamp, comprising:
    a. a container having a wick aperture, and one or more vent holes has an area between about 0.75 square millimeters and 75 square millimeters; and
    b. a wick protruding from the wick aperture, and adapted to carry oil from the container to a flame at an end of the wick.
2. The lamp of claim 1, wherein the vent holes are located on the upper third of the container.
3. The lamp of claim 1, wherein the vent holes are located on a relatively horizontal surface near the top of the container.
4. The lamp of claim 1, wherein the vent holes have an aggregate area of at least about 180 square mm.
5. The lamp of claim 1, wherein the container contains fuel comprising kerosene and about 2–10% by weight fragrance.
6. The lamp of claim 1, wherein the container contains fuel comprising an n-parafinic hydrocarbon and about 2–10% by weight fragrance.
7. The lamp of claim 1, further comprising a heat transfer system adapted to transfer heat from a flame to the contents of the container.
8. The lamp of claim 7, wherein the heat transfer system has a thermally conductive path having a cross-sectional area of at least about 9.4 square mm.
9. The lamp of claim 7, wherein the heat transfer system is adapted to heat fuel within the container to a temperature at least about 5° C. higher than the ambient temperature.
10. The lamp of claim 7, wherein the heat transfer system is adapted to heat fuel within the container to a temperature at least about 25° C. higher than the ambient temperature.
11. The lamp of claim 7, wherein the heat transfer system has a heat dissipating region comprising a tube surrounding the wick.
12. The lamp of claim 7, wherein the heat transfer system has a heat dissipating region comprising a conductive core disposed within the wick, having a cross sectional area of at least about 9.4 square mm.
13. The lamp of claim 7, wherein the heat transfer system has a heat absorbing region comprising a cylinder disposed around an upper end of the wick.

* * * * *